(12) United States Patent
Guy et al.

(10) Patent No.: US 9,132,150 B2
(45) Date of Patent: Sep. 15, 2015

(54) MAGNESIUM RICH DRINKING WATER

(75) Inventors: Ron Guy, Meitar (IL); Nikolay Fux, Beer Sheva (IL); Michael Bonan, Rechasim (IL); Eitan Dafny, Kiryat Ata (IL); Gideon Shikolsky, Kiryat Motzkin (IL)

(73) Assignee: Dead Sea Bromine Company Ltd., Beer Sheva (IL)

( * ) Notice: Subject to any disclaimer, the term of this patent is extended or adjusted under 35 U.S.C. 154(b) by 773 days.

(21) Appl. No.: 13/499,735

(22) PCT Filed: Oct. 14, 2010

(86) PCT No.: PCT/IL2010/000843
§ 371 (c)(1),
(2), (4) Date: May 1, 2012

(87) PCT Pub. No.: WO2011/045795
PCT Pub. Date: Apr. 21, 2011

(65) Prior Publication Data
US 2012/0201929 A1    Aug. 9, 2012

(30) Foreign Application Priority Data
Oct. 15, 2009   (IL) .......................................... 201568

(51) Int. Cl.
| A23L 1/304 | (2006.01) |
| A61K 33/10 | (2006.01) |
| A23L 2/52 | (2006.01) |
| A23L 2/54 | (2006.01) |

(52) U.S. Cl.
CPC ................ *A61K 33/10* (2013.01); *A23L 1/304* (2013.01); *A23L 2/52* (2013.01); *A23L 2/54* (2013.01); *A23V 2002/00* (2013.01)

(58) Field of Classification Search
CPC .......... A23L 1/304; A23L 2/54; A23K 33/10; A23V 2250/11; A23V 2250/161
USPC .................................. 426/66, 67, 74, 590, 477
See application file for complete search history.

(56) References Cited

U.S. PATENT DOCUMENTS

| 3,932,578 A | 1/1976 | Nishino et al. |
| 5,034,138 A | 7/1991 | Hatanaka |
| 6,048,553 A | 4/2000 | Beckett |

(Continued)

FOREIGN PATENT DOCUMENTS

| EP | 1460042 | 9/2004 |
| GB | 2089334 | 6/1982 |

(Continued)

OTHER PUBLICATIONS

WIPO International Preliminary Report on Patentability for PCT/IL2010/000843, 8 pages, mailed Apr. 26, 2012.
Azoulay A. et al.: J. Intern. Med. 16 (2001) 168-75.

*Primary Examiner* — Helen F Heggestad
(74) *Attorney, Agent, or Firm* — Roach Brown McCarthy & Gruber, P.C.; Kevin D. McCarthy (57) ABSTRACT

The invention provides a system for supplying a magnesium enriched drinking water, including circulating water through a bed of magnesium compound. The health-promoting water contains magnesium between 10 and 500 mg/liter, and further it may contain additional health promoting salts, while being sodium free.

9 Claims, 5 Drawing Sheets

(56) References Cited

U.S. PATENT DOCUMENTS

| | | | |
|---|---|---|---|
| 6,761,289 B1 | 7/2004 | Valentini | |
| 2003/0234212 A1 | 12/2003 | Ito et al. | |
| 2005/0255174 A1 | 11/2005 | Shelley | |

FOREIGN PATENT DOCUMENTS

| | | |
|---|---|---|
| JP | 62045396 A2 | 2/1987 |
| JP | 03106494 A2 | 5/1991 |
| JP | 2004082026 A2 | 3/2004 |
| WO | 2006/082898 A1 | 8/2006 |

| | Mg (ppm) | HCO3 (ppm) | Ratio | Molar Ratio | Mg (ppm) | Conduct µS | T | Water (l/h) | CO2 (l/h) | Recycle (l/h) |
|---|---|---|---|---|---|---|---|---|---|---|
| 22-1 | 32 | 101 | 3.16 | 1.26 | 32 | 230 | 17 C | 24 | No | No |
| 22-2 | 30 | 90.5 | 3.02 | 1.20 | 30 | 250 | 21 C | 24 | No | No |
| 22-3 | 190 | 988 | 5.20 | 2.07 | 190 | 1410 | 22.4C | 24 | 12 | No |
| 22-4 | 219 | 1118 | 5.11 | 2.03 | 219 | 1660 | 23 C | 26 | 13 | 400 |
| 22-5 | 253 | 1295 | 5.12 | 2.04 | 253 | 1920 | 22 C | 22 | 17 | 400 |
| 23-1 | 136 | 694 | 5.10 | 2.03 | 136 | 1000 | 22.5C | 34 | 18 | 200 |
| 23-2 | 138 | 708 | 5.13 | 2.04 | 138 | 1050 | 23 C | 34 | 22 | 200 |
| 23-3 | 146 | 748 | 5.12 | 2.04 | 146 | 1150 | 23.6 C | 34 | 22 | 200 |

Fig. 5

MAGNESIUM RICH DRINKING WATER

REFERENCE TO CO-PENDING APPLICATIONS

Priority is claimed as a 371 of international application number PCT/IL2010/000843, filed on Oct. 14, 2010; which claims priority to Israeli Patent application number 201568, filed on Oct. 15, 2009.

FIELD OF THE INVENTION

The present invention relates to a system for supplying a magnesium enriched water, comprising a closed flow circuit of an aqueous stream circulated through a bed of magnesium compound, and an open flow circuit of feeding fresh water into the stream and withdrawing enriched water out of it. Provided is drinking, health-promoting water fortified with magnesium.

BACKGROUND OF THE INVENTION

Magnesium belongs among four most plentiful metal elements in the body, together with calcium, potassium and sodium. The disorders associated with magnesium deficiency are complex and usually accompanied by multiple metabolic and nutritional disturbances. The clinical manifestations of magnesium deficiency is anorexia, nausea, vomiting, lethargy, weakness, personality change, tetany, and tremor and muscle fasciculation [The Merck Manual, $17^{th}$ Ed. (1999)]. Hypomagnesemia, the decrease of plasma magnesium, leads to neuromascular irritability. Magnesium deficiency may occur on loss of body fluids, excessive renal excretion, and may be associated with nutritional deficit, diarrhea, diabetes, pancreatitis, etc. Magnesium depletion may further lead to hypocalcemia and all the grave symptoms resulting therefrom. It was found that people who drink water that is deficient in magnesium generally appear more susceptible to a variety of medical conditions, mainly cardiovascular disorders.

Drinking water should preferably complete the magnesium supplied in food up to the daily required value. Recommended daily intake for adults is between 200 and 400 mg of magnesium [The Merck Manual, $17^{th}$ Ed. (1999)], and sometimes more. However, tap water frequently contains little magnesium; for example, the tap water available in big US cities often has less than 10 mg/l of magnesium [Azoulay A. et al.: J. Intern. Med. 16 (2001) 168-75]. Therefore, the modern principles of preventive medicine and healthy nutrition would require higher intake of magnesium, which can most easily be achieved by drinking mineral water or other bottled water with higher magnesium content. Many of the commercially available bottled waters have very low magnesium contents; moreover, some bottled waters, as well as some tap waters, contain too much sodium [ibid], which should be kept as low as possible in healthy diets. It is therefore an object of this invention to provide drinking water fortified with magnesium, and exhibiting low sodium content.

EP 1460042 relates to a process of producing potable water of higher magnesium content by dissolving a magnesium salt, preferably by mixing magnesium and potassium carbonates. The complex system comprises many compartments and separated pre-dissolving steps, whereas other cations, such as potassium, are incorporated. U.S. Pat. No. 6,761,289 relates to pressurized containers for preparing calcium and magnesium bicarbonate solutions, further containing additives such as sodium salts, under pressures ranging from 30 to 70 atmospheres. This high-pressure technology is too complex and provides modest magnesium concentrations. US 2005/0255174 relates to preparing magnesium bicarbonate, comprising mixing magnesium carbonate suspension in carbonated water. The complex system exhibits problems in regard to stirring the suspensions, dosing the substrate powders, and adjusting the pH. It is therefore another object of this invention to provide a method of supplementing drinking water with magnesium without the drawbacks of the prior art.

It is still another object of the invention to provide a method capable of supplying commercial volumes of drinking water fortified with magnesium.

It is a further object of this invention to provide a system for manufacturing drinking water with increased magnesium concentration but with low concentration of other cations.

It is a still further object of this invention to provide a non-pressurized, technologically simple, system for supplying health-promoting drinking water.

It is also an object of this invention to provide drinking water containing at least 500 mg/l magnesium bicarbonate.

Other objects and advantages of present invention will appear as the description proceeds.

SUMMARY OF THE INVENTION

The present invention provides a process for producing magnesium-enriched drinking water, comprising the steps of i) providing a bed of magnesium compound; ii) pumping an aqueous stream through said bed; and iii) injecting carbon dioxide ($CO_2$) into said aqueous stream; thereby obtaining an aqueous solution of magnesium bicarbonate. The process according to the invention preferably comprises measuring the electrical conductivity in said aqueous stream. Said bed is usually closed in a flow-through reactor, wherein said aqueous stream dissolves said $CO_2$, and further also dissolves said magnesium compound as it flows through said bed, yielding said solution of magnesium bicarbonate. The reactor may have the form of a chromatographic column with suitably located inlets and outlets. In a preferred embodiment of the process according to the invention, said solution of magnesium bicarbonate is recirculated through said bed, wherein said aqueous stream defines a closed circuit, comprising said bed and further a pump ensuring a desired circulation flow rate. Said circuit comprises an inlet through which fresh water is fed into said aqueous stream, and an outlet through which said solution is taken out of said stream and collected, providing magnesium-enriched drinking water, wherein said inlet and said outlet define an open circuit further optionally comprising one or two pumps ensuring a desired feeding flow rate which is lower than said desired circulation flow rate; said inlet and outlet may be located, for example, outside said reactor. Said $CO_2$ is injected from a cylinder through an injecting means ensuring fine gas dispersal in said aqueous stream, and comprising a vent ensuring a desired gas flow rate which is greater than, or equal to, the stoichiometric amount needed for the reaction of water, $CO_2$, and said magnesium compound to provide said magnesium bicarbonate; the excess may be, for example, at least 10%. Said circulation flow rate is greater than said feeding flow rate, for example approximately ten times greater. Said open circuit further comprises an inlet through which another component is incorporated into said magnesium enriched drinking water. Said other component may be selected, for example, from the group consisting of salt, health-promoting material, salts, minerals, taste or flavor-rendering material, or disinfectants. It should be noted that magnesium bicarbonate does not render any flavor or taste to water. All the materials being in contact with said aqueous stream should be acceptable for contacting potable water for human consumption. In one aspect of the invention, no sodium is incorporated into the aqueous stream, and essentially sodium-free drinking water is provided, or alternatively sodium is kept at a low concentration, such as about 10 ppm or less. In a preferred embodiment of the invention, provided is a process for producing magnesium-enriched drinking water comprising magnesium at a controlled concentration comprising i) providing a bed of magnesium oxide (MgO); ii) pumping an aqueous stream through said bed of MgO; and iii) injecting carbon dioxide ($CO_2$) into said aqueous stream; thereby obtaining an aqueous solution of magnesium bicarbonate at a controlled concentration. The concentration may be at least 0.06 g/l. The invention can provide drinking water enriched with magnesium in a concentration of up to 250 ppm. In various situations, and according to the need, the invention can provide drinking water with contents of magnesium higher than 250 ppm. The invention can increase the magnesium content in water from any value to any other desired value; for example, the invention can be used to increase the magnesium content in water containing about 10 ppm or 30 ppm magnesium which may be provided from deionized water, or it can be used to provide drinking water containing up to 50 ppm magnesium or 100 ppm magnesium or up to 130 ppm magnesium, which may be provided from waters having low salt contents.

Said magnesium concentration in the magnesium-enriched water according to the invention may contain dissolved magnesium at a concentration of at least 200 ppm. Said dissolved magnesium may have a concentration of about 250 ppm.

The invention is directed to an apparatus and a system for manufacturing health-promoting, magnesium-enriched, drinking water comprising i) an essentially closed aqueous stream circuit, comprising a bed of magnesium compound through which said aqueous stream flows and a pump ensuring a desired circulation flow rate; ii) an injection means for incorporating carbon dioxide ($CO_2$) to said aqueous stream; iii) an open flow circuit comprising an inlet for feeding fresh water into said aqueous stream and an outlet for taking magnesium-enriched water out of said aqueous stream, and further a pumping means ensuring a desired feeding flow rate which is lower than said desired circulation flow rate; iv) means for supplying fresh portions of said magnesium compound to said bed; conductometer for continuous measuring the electrical conductivity in said aqueous stream; and v) regulation unit receiving conductivity data from said conductometer and managing said feeding flow rate and optionally said circulation flow rate to ensure the desired amount of dissolved magnesium in said aqueous stream. The apparatus and system according to the invention may comprise processing means for adding various useful components to the aqueous intermediate or to the final product. Such component may serve in disinfecting the intermediate or product, in adding additional salts, in adding health-promoting minerals and salts, in adding a desired taste or flavor to the product. The apparatus of the invention comprises, in a preferred aspect of the invention, a bed of magnesium oxide, such as fused MgO.

The invention provides drinking, health-promoting water comprising at least 10 mg/l, and preferably at least 200 mg/l magnesium. The invention may provide magnesium-enriched drinking water comprising about 500 mg/l magnesium or more. The drinking water according to the invention may comprise magnesium bicarbonate at a concentration of from 30 mg/l to 3000 mg/l, or more. The invention may provide healthy drinking water enriched in magnesium, optionally free of sodium ions, and optionally further comprising other additional health promoting salts. Such salts may comprise iodine, fluorine, calcium, and other elements. The healthy drinking water may be packaged in any portable means, with various additives, to provide health-promoting mineral waters.

BRIEF DESCRIPTION OF THE DRAWINGS

The above and other characteristics and advantages of the invention will be more readily apparent through the following examples, and with reference to the appended drawings, wherein:

FIG. 4A relates to tap water, and FIG. 4B to deionized water.

DETAILED DESCRIPTION OF THE INVENTION

It has now been found that a highly magnesium-enriched water for human consumption can be obtained in an easily manageable process on an industrial scale, using dissolution of magnesium oxide by carbonized water in a flow-through reactor. Further it has been found that the dissolution process is more efficient if a second circuit is incorporated into the system, beside the circuit which feeds fresh water and withdraws the product, namely a circuit comprising a rapid recirculation of aqueous stream through the bed of MgO. When a bed of magnesium compound, or shortly a bed, is related to when describing this invention, intended is a bed of granular magnesium oxide that has been produced by fusion, sintering or calcination of magnesium oxide, preferably at a temperature above 1200° C., or a bed of granular or tablet form comprising magnesium hydroxide or magnesium carbonate.

The invention thus relates to a system and process for producing magnesium-enriched drinking water, comprising at least two circuits, a closed circuit comprising recirculation of the magnesium containing water through the bed of magnesium compound, preferably MgO, and an open circuit, linked to the closed one, comprising the flow of fresh water into the system and withdrawing the magnesium-enriched water from the system. For the purpose of this description, when a mass flow comprising a closed curve is involved, the term "closed circuit" is employed, while in other cases, the term "open circuit" is employed. Another circuit, linked to said closed circuit, comprises the flow of carbon dioxide from a cylinder to the aqueous stream, via an inlet into the aqueous stream, preferably via a vent situated near to the bed. The whole process can be automated by utilizing the measurement of electrical conductivity, which can provide feedback for regulating flow rates in the circuits.

In a further aspect, the invention provides drinking water which is enriched with magnesium. It should be noted that the magnesium contents of tap water in US cities are usually between 1 and 10 mg/l (1-10 ppm), the high values being under 30 ppm. The magnesium contents of bottled waters in US and Europe never pass 130 ppm [Azoulay A. et al.: J. Intern. Med. 16 (2001) 168-75]. The invention can provide drinking water containing magnesium at a concentration of from 10 ppm to 200 ppm. The invention, in another aspect, can provide drinking water containing magnesium at a concentration higher than 200 ppm. In a preferred embodiment, the invention provides health-promoting drinking water having a magnesium content of from 150 to 250 ppm. In other preferred embodiment, the invention provides a magnesium rich water comprising from 200 to 300 ppm magnesium. In still another preferred embodiment, the invention provides drinking water comprising magnesium at a concentration of from 150 to 300 ppm, optionally comprising calcium, and optionally further comprising a low sodium content. A sodium content lower than 50 ppm is considered as a low sodium content herein. Calcium may be incorporated into the magnesium-enriched water or may be present before enriching water with magnesium according to the invention. In drinking water of the invention, calcium may be present at a concentration of from 1 to 100 ppm as in US tap waters, or from 100 to 600 as in some mineral waters. The invention may supply health-promoting drinking water types fortified with magnesium and other elements selected from calcium, iron, potassium, iodine, fluorine, zinc, or anions, such as phosphate. The water can be packaged in any type of portable means, the product being possibly fortified with vitamins.

The process and the apparatus of the invention comprise dissolving of magnesium oxide in a flow-through reactor. In a preferred embodiment, the reactor comprises a bed of MgO, through which a carbonized aqueous stream flows. In a preferred embodiment, the aqueous stream is pumped and circulated through the bed of MgO in a first flow circuit (closed circuit), and fresh water is fed to and withdrawn from the stream in a second flow circuit (open circuit), wherein the flow rate through the first circuit is greater than through the second circuit. In one arrangement, tested in pilot, the ratio of the flow rates was 10.

The invention will be further described and illustrated in the following examples.

EXAMPLES

Materials and Equipment

Deionized water was used. Tap water was used in some of the demonstrations. Fused MgO screened on 1 mm sieve was used.

Figure 1:
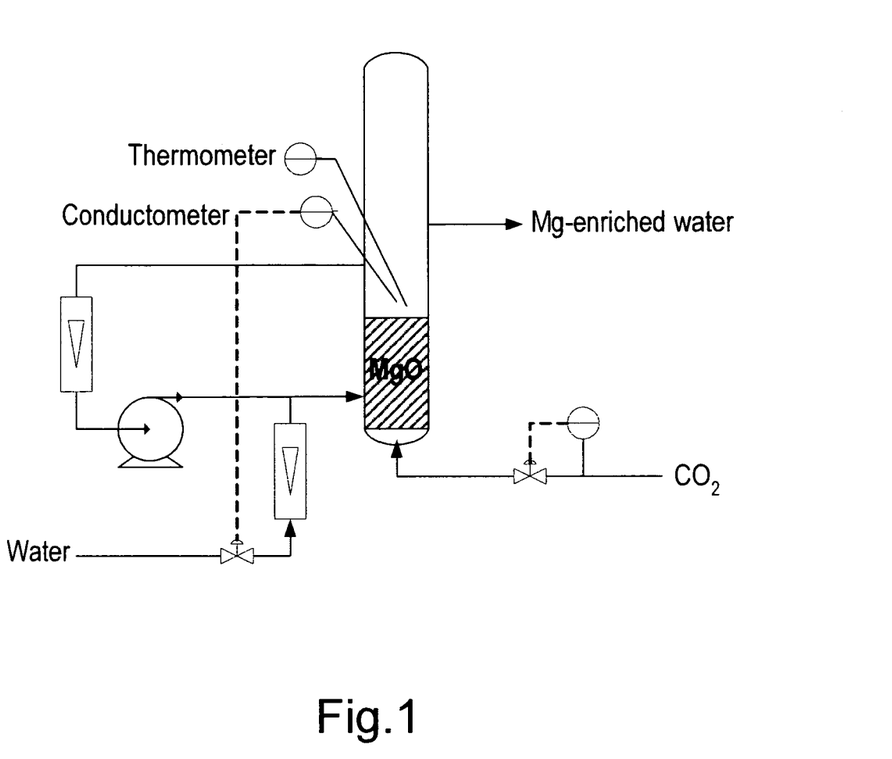
FIG. 1. is a scheme of the equipment in producing magnesium-enriched water in one embodiment of the invention.

A PVC column of 10 cm diameter and 150 cm height was equipped with five taps at different heights for allowing evaluation of the influence of the residence time of the liquid in the column. The column was filled with 3.5 kg of fused MgO to a height of 32 cm. The water was fed through the column at various rates. $CO_2$ was fed from a cylinder and the flow was controlled by a valve, the inlet of the $CO_2$ pipe was situated at the bottom of the column. A recycle stream increased the magnesium yield in the solution. The scheme of the system used is shown in FIG. 1.

Figure 4:
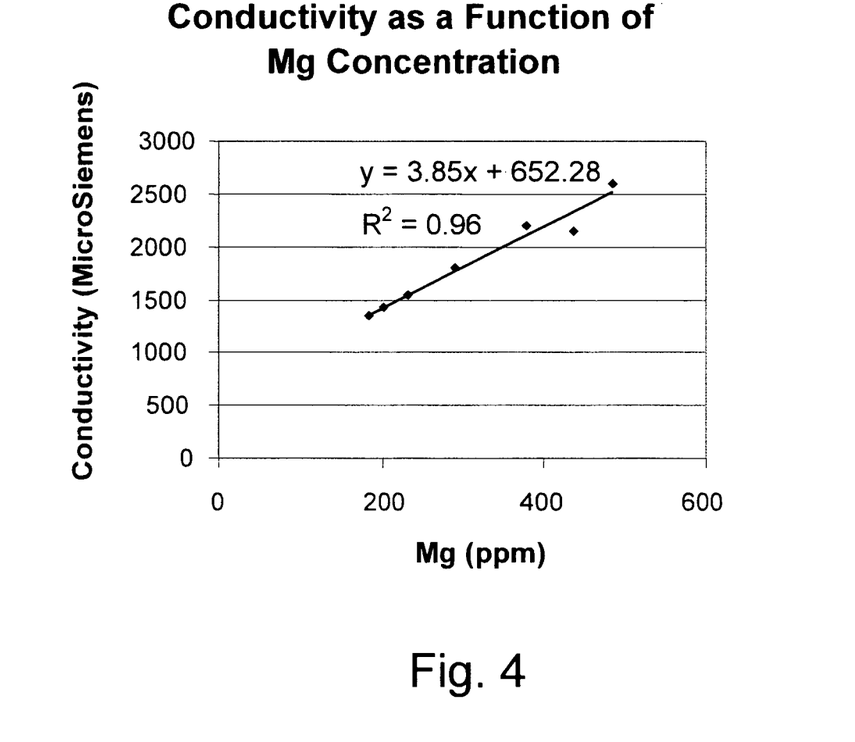
FIG. 4. is a graph showing conductivity as a function of magnesium concentration in the present system.
Figure 5:
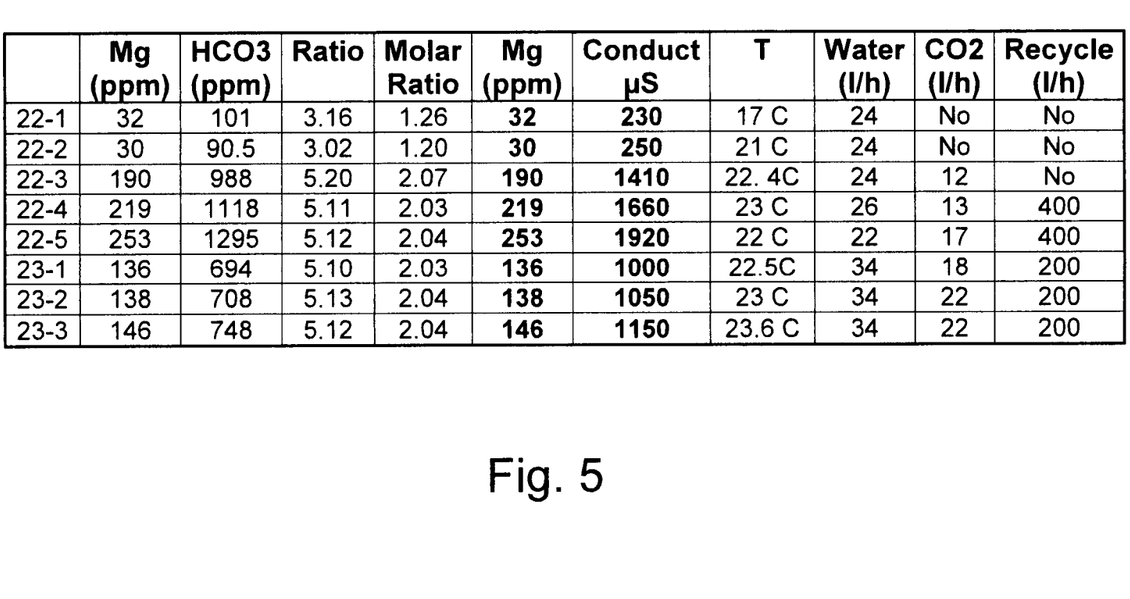
FIG. 5. comprises Table 1.

Conductivity can be advantageously used for determining magnesium concentration in the solution (FIG. 4). The tests showed that the flow rate of water through the column in the range of 6 to 48 l/h was suitable; 30 l/h was usually applied. The recycle flow increased the MgO dissolution rate: it was generally about 200 l/h. Increase of the $CO_2$/water ratio increased the magnesium dissolution rate to a limiting value, but, on the other hand, the excess $CO_2$ was unnecessarily lost. The minimum $CO_2$ quantity for dissolving Mg(O) to a concentration of 250 ppm with water feed of 24 l/h was about 12 l/h $CO_2$ (see also the Table in FIG. 5). Usually, 12 l/h was fed, a quantity approximately corresponding to slightly more than the stoichiometry. The height of the solids was kept constant at the beginning of the tests, at about 30 cm; this height decreased with the progress of the reaction reaching about half of the initial height in the last long run test.

Feeding $CO_2$ at pressures greater than atmospheric pressure gives higher magnesium dissolution rates, but the increase in magnesium concentration with $CO_2$ pressure is asymptotic and involves reduced efficiency in $CO_2$ consumption. However, the system of the invention enables enriching water with magnesium also under higher pressures of $CO_2$.

Control of the Process

Figure 2:
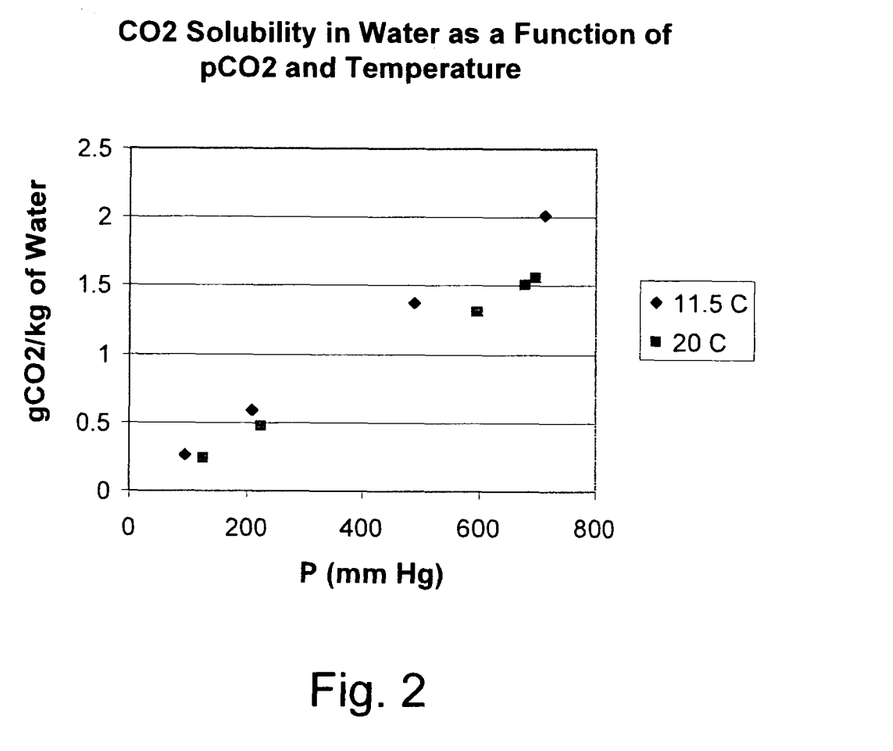
FIG. 2. is graph showing solubility of $CO_2$ at two temperatures determined under the present conditions.
Figure 3:
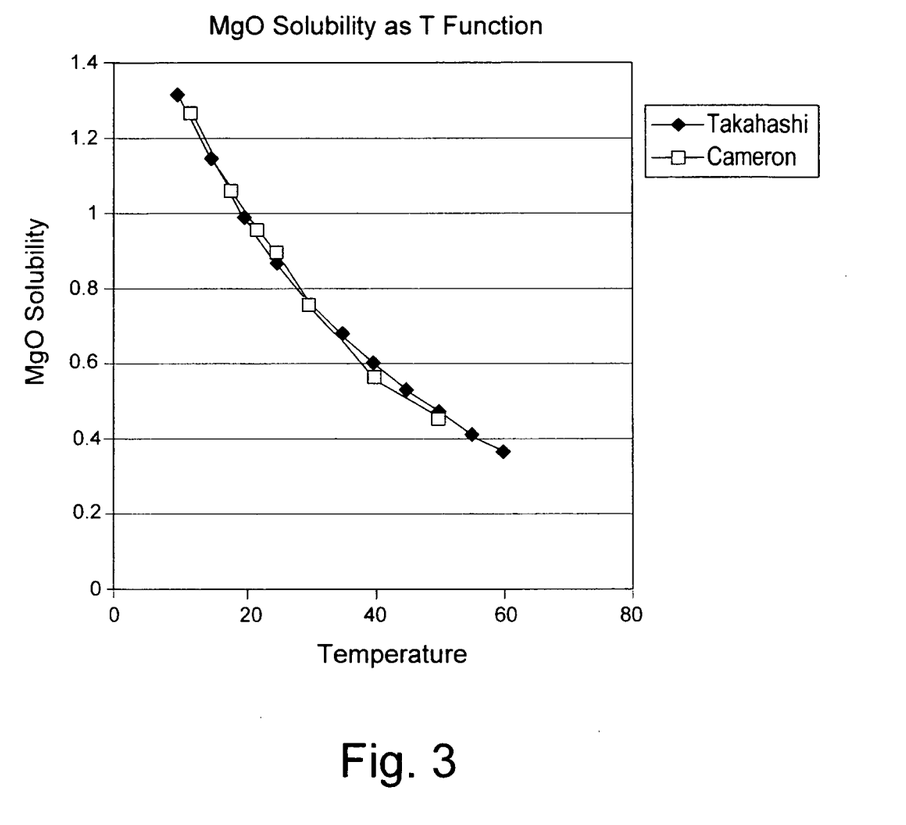
FIG. 3. is a graph showing solubility of MgO as a function of the temperature.

The conductivity was measured. The flow of water, and so also the residence time, was controlled by the conductivity measurement. The solubility of $CO_2$ in water increases with the pressure of $CO_2$ and decreases with the temperature as shown in FIG. 2. The MgO is solubilized according to the equation:

$$MgO + 2CO_2 + H_2O \rightarrow Mg(HCO_3)_2 \qquad (1)$$

The linear relationship between the magnesium concentration and conductivity was determined as shown in FIG. 4; calibration with tap water (conductivity 650 μSiemens without added magnesium) is shown, and with deionized water; the measurements are shown for the range relevant for the process, i.e. around 200 ppm magnesium. The influence of the temperature on the conductivity was about 1.8%/1° C. This influence was neutralized in the calibrated correction of the results.

The following parameters are of importance in determining the rate of production of magnesium-enriched water:

- Water flow: The water flow is related to the residence time, which appears as the dominant parameter.
- Recycle: Implementation of a recycle stream allowed stabilizing the measurement of the conductivity and thus the process. A large recycle (about 10:1 ratio, namely the ratio of the recycle flow rate and fresh water feeding flow rate) was further required for reaching the 250 ppm magnesium concentration.
- The ratio $CO_2$/water must be such that there was a slight excess of $CO_2$ versus the stoichiometry of the reaction expressed by equation (1). Further increasing $CO_2$ had only a weak effect.
- Temperature: The present examples relate to water in the temperature range 10 to 25° C. The solubility of MgO at a given pressure of $CO_2$ decreases with the temperature, but the saturation with $CO_2$ is not reached under usual working conditions anyway. Under these conditions, the influence of the temperature was such that more magnesium was dissolved at a higher temperature—about 3.6% more per 1° C. The effect of the temperature on the conductivity was supposedly "neutralized" by the calibrated measurement system.
- Height of the solids in the column: The parameter is related to the residence time, but it also affects the hydrodynamic behavior. The weight ratio of about 5 between $HCO_3$ and magnesium (see Tab. 1) corresponds well to the theoretical molar ratio of 2 (see equation (1) above).

Extended Operation of the Invention

The robustness of the invention was evaluated by monitoring the above parameters under conditions when the temperature and the flow were not constant. The recycle was kept constant at 200 l/h. After correction of the effect of the temperature, the calculated magnesium concentration was relatively stable, around 250 ppm.

The corrected conductivity remained very stable. The conductivity controlled the flow of water, and thus the residence time, keeping them constant. The magnesium concentration measured was: 280±3 ppm when the conductivity was in the range 1960±20 μSiemens (the temperature was stable, about 27° C.).

The test was continued by closing the recycle. The flow rate of the water was reduced to compensate for the lowered level of MgO (about half of the MgO fed was dissolved). It was confirmed that the process is mainly controlled by the residence time. Closing the recycle necessitated a strong decrease of the flow.

Both residence time and recirculation has important effects on the process. The rate of magnesium dissolution is much lower without recycle, it seems that the recirculation increases turbulence in the system and consequently the rate of diffusion from the surface of the solids. Further increase of the recycle flow did not improve the rate of MgO dissolution. The increase of the $CO_2$/water has a weaker influence, and a practical design of the process may relate the $CO_2$ flow directly to the water flow. The effect of the temperature can be "neutralized" by an efficient control by the way of the measurement of the conductometry, with temperature calibration.

At the end of the last long run test, the weight of MgO was half of the initial one. The maximal size of the particles which can be entrained by the flow was estimated by using the Stokes equation ($F=6\pi r\eta v$) to be about 70 μm diameter for spherical particles and for 200 l/h in the present system. It would mean that for an initial size of about 1000 μm, more than 99.9% of the MgO can be dissolved before entrainment. The concentration of insoluble impurities in the raw material is very low; they may be eliminated by the use of a sudden increase of the flow rate and removing them on the polishing filter at the exit of the column.

The pilot employed a column of 10 cm diameter, which was filled to a height of about 30 cm, but further considered was a column filled to the height of 1.2 m. The feasibility of the process was proved: the main parameter is the residence time of the water in the column and a recycle flow is required (10:1 ratio between the recycle and the feed in the present work), while the influence of the ratio $CO_2$/water is lower and increasing the temperature leads to an increase of the MgO dissolution of about 3.5%/1° C. increase. The design for a larger unit, as a basis of the scale-up to an industrial process, can be provided by one skilled in art.

While this invention has been described in terms of some specific examples, many modifications and variations are possible. It is therefore understood that within the scope of the appended claims, the invention may be realized otherwise than as specifically described.

The invention claimed is:

1. A process for producing magnesium-enriched drinking water, comprising
   i) providing a bed of magnesium oxide obtained by fusion, sintering or calcination enclosed in a flow-through reactor;
   ii) pumping an aqueous stream through said bed;
   iii) injecting carbon dioxide ($CO_2$) into said aqueous stream, wherein said aqueous stream dissolves said $CO_2$ and said magnesium oxide thereby yielding an aqueous solution of magnesium bicarbonate, the magnesium bicarbonate solution rapidly circulates through said bed, and wherein said aqueous stream defines a closed circuit, the circuit comprising said bed and a pump ensuring a desired circulation flow rate wherein said rapid circulation increases the turbulence in said aqueous stream within the bed whereby increasing dissolution of said magnesium oxide from said bed;
   iv) providing said circuit with an inlet through which fresh water is fed into said aqueous stream and with an outlet through which said solution is taken out of said stream and collected, wherein said inlet and said outlet define an open circuit into which said water is fed with a desired feeding flow rate; and
   v) measuring the electrical conductivity in said aqueous stream and regulating said circulation flow rate and said feeding flow rate according to the results of said conductivity measurement, whereby achieving a desired magnesium concentration in said aqueous stream corresponding to a concentration of magnesium bicarbonate of at least 0.06 g/l.

2. The process according to claim 1, wherein said circuit comprises an inlet through which fresh water is fed into said aqueous stream, and an outlet through which said solution is taken out of said stream and collected, providing magnesium enriched drinking water, wherein said inlet and said outlet define an open circuit further optionally comprising one or two pumps ensuring a desired feeding flow rate which is lower than said desired circulation flow rate.

3. The process according to claim 1, wherein said $CO_2$ is injected from a cylinder through an injecting means ensuring fine gas dispersal in said aqueous stream, and a desired gas flow rate which is equal to or greater than a stoichiometric amount needed for the reaction of water, $CO_2$, and said magnesium oxide to provide said magnesium bicarbonate.

4. The process according to claim 2, wherein said circulation flow rate is approximately ten times greater than said feeding flow rate.

5. The process according to claim 2, wherein said open circuit further comprises an inlet through which a further component is incorporated into said magnesium enriched drinking water, selected from the group consisting of calcium, iron, potassium, iodine, fluorine, zinc, vitamins, taste-rendering materials, and flavor-rendering materials.

6. The process according to claim 1, wherein all used raw materials are acceptable for contacting potable water for human consumption, and further they are essentially sodium free.

7. The process according to claim 1 for producing magnesium-enriched drinking water, wherein said desired magnesium concentration is at least 10 ppm.

8. An apparatus for producing magnesium-enriched, drinking water comprising
   i) an essentially closed aqueous stream circuit, the circuit comprising a bed of magnesium oxide obtained by fusion, sintering or calcination through which said aqueous stream flows and a pump ensuring a desired rapid circulation flow rate which increases the turbulence in said aqueous stream within the bed whereby increasing dissolution of said magnesium oxide from said bed;
   ii) an injection means for incorporating carbon dioxide ($CO_2$) into said aqueous stream;
   iii) an open flow circuit comprising an inlet for feeding fresh water into said aqueous stream and an outlet for taking magnesium-enriched water out of said aqueous stream, and further a pumping means ensuring a desired feeding flow rate which is lower than said desired circulation flow rate and which ensures a desired residence time of said magnesium-enriched water in said bed;
   iv) means for supplying fresh portions of said magnesium compound to said bed;
   v) conductometer for continuously measuring the electrical conductivity in said aqueous stream; and
   vi) regulation unit receiving conductivity data from said conductometer and managing said feeding flow rate and said circulation flow rate to ensure the desired amount of dissolved magnesium in said aqueous stream;

wherein said managing the feeding flow rate and said circulation flow rate ensures the constant magnesium concentration in said magnesium-enriched water taken out of said outlet.

9. The apparatus according to claim 8 for producing health-promoting, magnesium-enriched, drinking water, wherein said bed comprises fused or sintered magnesium oxide.

* * * * *